United States Patent
Wohlrab et al.

Patent Number: 5,346,692
Date of Patent: Sep. 13, 1994

[54] NAIL LACQUER FOR THE TREATMENT OF ONYCHOMYCOSIS

[75] Inventors: Wolfgang Wohlrab; Katrin Wellner, both of Halle, Fed. Rep. of Germany

[73] Assignee: Roehm Pharma GmbH, Weiterstadt, Fed. Rep. of Germany

[21] Appl. No.: 43,927

[22] Filed: Apr. 8, 1993

[30] Foreign Application Priority Data

Apr. 10, 1992 [DE] Fed. Rep. of Germany ....... 4212105

[51] Int. Cl.$^5$ .............................................. A61K 7/043
[52] U.S. Cl. ...................................................... 424/61
[58] Field of Search .......................................... 424/61

[56] References Cited

U.S. PATENT DOCUMENTS

| 4,180,058 | 12/1979 | Brem | 128/897 |
| 4,721,724 | 1/1988 | Stettendorf et al. | 514/396 |
| 4,957,730 | 9/1990 | Bohn et al. | 424/61 |
| 5,120,530 | 6/1992 | Ferro et al. | 424/61 |

FOREIGN PATENT DOCUMENTS

| 0204230 | 12/1986 | European Pat. Off. . |
| 0226984 | 7/1987 | European Pat. Off. . |
| 298271 | 1/1992 | European Pat. Off. . |
| 279623 | 11/1990 | Japan . |
| 2202743 | 10/1988 | United Kingdom . |
| 8702580 | 5/1987 | World Int. Prop. O. . |

OTHER PUBLICATIONS

Chemical Abstracts, vol. 96, No. 20, 1982, AM-168622k.

*Primary Examiner*—Thurman K. Page
*Assistant Examiner*—Amy L. Hulina
*Attorney, Agent, or Firm*—Oblon, Spivak, McClelland, Maier & Neustadt

[57] ABSTRACT

The invention relates to a nail lacquer for treating onychomycosis, comprised of a film-forming agent, an antimycotically active substance, and urea, wherewith the antimycotically active substance and the urea are liberated from the lacquer when the lacquer is applied. A preferred formulation comprises cellulose derivative(s) as film former(s), clotrimazole as the antimycotic (present in the amount of 5–30 wt. % based on the weight of the non-volatile components), urea (present in the amount of 15–60 wt. % based on the weight of the non-volatile components), and dibutyl phthalate as a plasticizer, in a solvent mixture comprised of acetone and ethanol.

13 Claims, No Drawings

NAIL LACQUER FOR THE TREATMENT OF ONYCHOMYCOSIS

BACKGROUND OF THE INVENTION

Field of the Invention

The invention relates to a nail lacquer (nail polish) for treating onychomycosis, which lacquer is comprised of a film-forming agent, an antimycotically active substance or mixture of antimycotically active substances, and urea, wherein the antimycotically active substance and the urea are liberated from the lacquer when applied to the nail to be treated.

Discussion of the Background onychomycosis is a disease of the nails of the fingers and toes caused by *Epidermophyton floccusum*, by several species of Trichophyton or by *Candida albicans*. The nails become opaque, white, thickened, fragile and brittle. It is acknowledged that the therapy of onychomycosis is difficult and protracted. Oral therapy with antimycotics requires months of administration, has only a 50% success rate, and must be closely monitored for side effects.

As supplemental local measures, mechanical ablation of affected nail areas, and topical treatment with antimycotic-containing medicinal preparates, are used in practice. Extraction of the nail, particularly where multiple nails are affected, is frequently not an acceptable option from the standpoint of the patient (see Mensing, H., and Walther, H., 1989, "Dermatologie in der taeglichen Praxis", Gustav-Fischer-Verlag, Stuttgart-New York, pp. 239 ff.).

Topical use of generally suitable preparates is ineffective, because of inadequate penetration through the nail keratin. The proposal which has been made of drilling small holes in the nail to afford the fungicide access to the layers below would seem to be costly (Brem, J., 1981, "Effective topical method for therapy of onychomycosis", *Cutis*, 27, 69).

For some time, methods have been used which employ a specially formulated antimycotic-containing medicine. Treatment of nails with a high-percentage solution of urea and sodium metabisulfide leads to cleavage of the disulfide linkages and hydrogen bridges of the keratin, enhancing the penetration by the fungicide (see Barlow, J. E., and Chattaway, F. W., 1955 *Lancet II*, 1269; and Ramesh, V., et al., 1983 *Int. J. Dermatol.*, 22, 148).

Another preparate which has proven effective in practice is a potassium iodide ointment having a lanolin base. However, the preparate has the drawbacks of granularity (attributable to a recrystallization phenomena) and staining (due to liberation of iodide) (Kleine-Watrop, H. E., 1979 *Dermatol. Mon. Schr.*, 165, 137).

Recent practice has been to use ointments with a urea content of up to 40 wt. %, for onycholysis. Such formulations do not attack healthy nail material. Preparations containing 30-40 wt. % of urea in an ointment based on wool wax alcohol or a similar base are frequently formulated and prescribed by dermatologists. Products of this type are also available commercially. The ointment is applied to the nail and covered with a plaster, then the softened nail material is removed after c. 24 hr with a scraper.

A number of patent applications describe topical nail lacquers.

JP-A 89-99,159 and JP-A 87-266,059 describe nail lacquers which comprise an antimycotic agent, polyvinyl acetate as a film former, and a volatile solvent component. The film which forms on the nail is removed after 6 hr. When 3 patients were treated repeatedly over a period of 3 mo, there was complete healing of nail trichophytosis.

DE 3,544,983 describes nail coatings comprising a water-insoluble film forming agent and an antimycotic agent.

In PCT App. WO 87 02 580 nail lacquers are described which contain a hydrophilic film forming agent with $\overline{M}w < 550$ Daltons and an antimycotic agent. After the nail lacquer is applied, a non-sticky transparent film forms within 3 min. It is possible to cure onychomycosis within 8 mo with 2 applications per week.

EP 298,271 describes nail lacquers comprising at least one water-insoluble film forming agent and at least one antimycotically active substance from the group tioconazole, econazole, oxiconazole, miconazole, tolnaftate, and naftifine hydrochloride. The nail lacquers are preferably employed as therapeutic nail lacquers which contain an amount of the antimycotic agent sufficient to kill the Dermatophytes responsible for the onychomycosis.

In PCT App. WO 88 08 884, a formulation for the topical treatment of onychomycosis is described which comprises an antimycotic agent, an antiseptic, and a film forming agent. Treatment of onychomycosis for 28 weeks was successful.

Despite the favorable therapeutic effects of urea-containing ointments, the treatment is accompanied by unpleasantness for the patient which can be reduced by a formulation in the form of a nail lacquer. The ability to apply a lacquer to a locally circumscribed area on the nail enables one to avoid irritation of the surround skin. In addition, the application of a plaster is obviated, because the lacquer forms a solid film on the nail being treated.

On the other hand, there is the question of how rapidly (if at all) the antimycotic agent is released to the nail, and how quickly it reaches the locations in the nail which are affected by onychomycosis.

Based on the state of the art set forth above, and the above-mentioned requirements, the underlying problem of the invention is to devise a nail lacquer for treating onychomycosis which can be applied topically to the affected nail area, as an easily removable film, which provides good liberation of the active principle, and which affords good diffusion of the antimycotic active principle into the regions of the nail which are affected by onychomycosis, without attacking healthy nail material.

SUMMARY OF THE INVENTION

It has been found that this problem is solved in outstanding fashion by nail lacquers comprising a) a film former, preferably a cellulose derivative,
b) an antimycotically active substance, preferably clotrimazole,
c) urea, and
d) optionally plasticizers, in a solvent mixture comprised of
   (i) a component A which absorbs or is absorbed by the film former, and
   (ii) a component B which dissolves the active principles (urea and the antimycotic).

The present invention also relates to a method of treating onychomycosis by applying the above described nail lacquer.

DETAILED DESCRIPTION OF THE PREFERRED EMBODIMENTS

The Film Forming Agent

The film foxing agents are pollers which form coherent films as the solvent evaporates; these films are permeable to the antimycotic active principle and the urea.

Thus, e.g., polymer dispersions may be used wherein drying is carried out at temperatures above the glass transition temperature (Tg) and the dispersions then form continuous polymer films. If a substrate such as a fingernail is coated with such a polymer dispersion, and drying is carried out by evaporation of the solvent, the result is a film-coated surface (see Kirk-Othmer, 1981, "Encyclopedia of Chemical Technology", 3rd Ed., Vol. 14, J. Wiley, New York, p. 30).

Such polymer dispersions may be comprised of polyvinyl acetate; mixed polymers of vinyl acetate and acrylic acid; mixed polymers of (meth)acrylic acid and (meth) acrylate esters, polyvinyl acetate, or polyvinyl butyryl.

Preferred film formers are cellulose derivatives, such as cellulose acetate phthalate, cellulose acetate butyrate, cellulose acetate propionate, cellulose nitrate, cellulose sulfate, ethylcellulose, and cellulose acetate. For the manufacture and the film forming properties of these cellulose derivatives, see Kirk-Othmer, 1979, loc-cit., Vol. 5, pp. 70-163.

The Combination of an Antimycotic and Urea

The inventively employed antimycotics are preferably imidazole derivatives, such as Tioconazole:

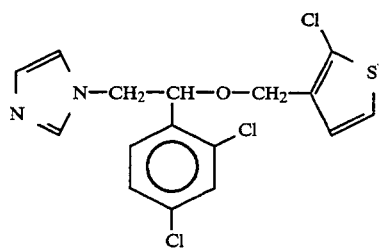

(I)

Econazole:

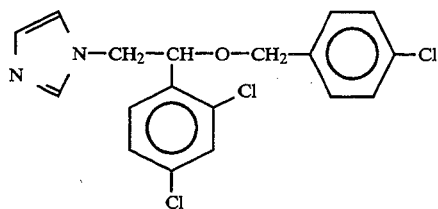

(II)

Oxiconazole:

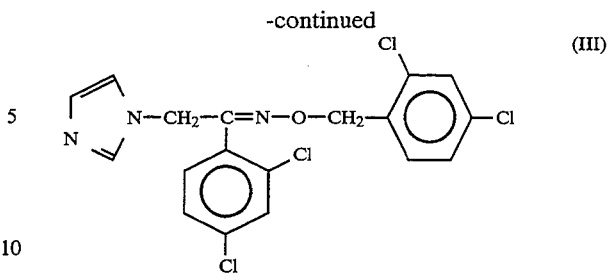

(III)

Miconazole:

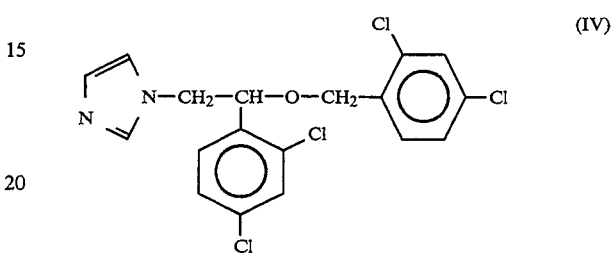

(IV)

and, particularly preferably, Clotrimazole:

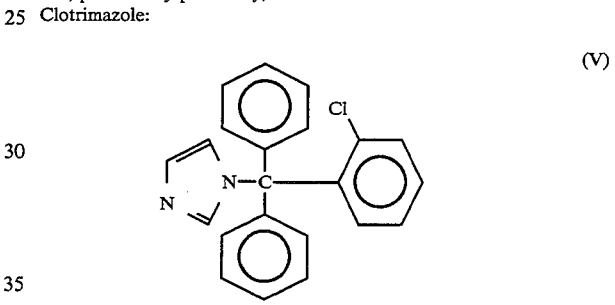

(V)

Other suitable antimycotic compounds are bifonazole, butaconazole, chlordantoin, chlormidazole, cloconazole, enilconazole, fenticonazole, isoconazole, ketoconazole, omoconazole, oxiconazole nitrate, and sulconazole. The preparation of these antimycotic compounds can be found by reference to the appropriate passages from the Merck Index, 11th Edition.

The urea employed in combination with the antimycotic is known for its keratolytic action (EP 298,271). Therefore it was to be expected that strong keratolysis would occur with urea in the proportions used according to the invention, namely 10–60 wt. %, preferably 15–60 wt. % urea more preferably 20–50 wt. %, in combination with 1–50 wt. %, preferably 5–30 wt. % more preferably 10–20 wt. % antimycotic (% by weight figures are based on the nonvolatile components of the nail lacquer), which will soften healthy as well as onychomycotic affected areas of the nail. Concerning the keratolytic action of urea and the optimum set of properties of combinations of urea and pharmaceutical active principles, see Wohlrab, W., 1981 Dermatol. Monatschrift, 167, 188–191. It is pointed out there that the improved effectiveness of externally applied medicines when urea is added comes about by the additive effect of a number of factors, and is not obvious to one skilled in the art. Surprisingly, the urea and the antimycotic are liberated in measured fashion onto the nail from the film which forms, in such a way that the healthy parts of the nail do not undergo substantial keratolysis. This enables highly targeted and localized treatment of onychomycosis, with maximum retention of healthy nail material.

The Solvent for the Film Former(s), Antimycotic, and Urea

Solvents for the inventive lacquer, which may be present in amounts of at least 50 wt. %, preferably at least 70 wt. %, particularly preferably at least 80 wt. % (based on the weight of the lacquer formulation), may be, e.g., substances used in the cosmetics industry. such as alcohols, ketones, ethers, aromatic hydrocarbons (e.a. toluene), or esters (e.a. ethyl acetate). Preferred are combinations of solvents wherein the components have a good uptake of the film forming agent(s) and good solubility for the active principles (the antimycotic and urea).

Particularly preferred are mixtures of ketones and alcohols, e.g. acetone/ethanol mixtures (in the case of cellulose acetate as the film former, urea as the keratolytic active principle, and clotrimazole as the antimycotic active principle).

At the same time, the solvent (or preferably the solvent mixture) must be sufficiently volatile to provide drying times of the nail lacquer of a few minutes or less. Other factors beside drying time which are of importance are flow characteristics in application, rate of film-forming, viscosity, and other significant lacquer parameters. To provide uniform evaporation, preferably the solvent mixture is comprised of a mixture of solvents having different boiling points. Advantageously, solvents in this connection have boiling points between 40° and 150° C.

The mixture of solvent(s), film former(s), urea, and antimycotic preferably also contains plasticizers, such as, e.g., triacetin, propylene glycol, castor oil, camphor, or phthalates: particularly preferred is dibutyl phthalate in an amount of from 5–30 wt. % preferably 10–20 wt. % based on non-volatile components. The plasticizers influence the liberation of the urea and the antimycotic, and therefore should be adjusted individually. The combination of film former, urea, antimycotic, and any plasticizers is referred to as "the non-volatile components".

Additional non-volatile adjuvants for nail lacquers familiar in the cosmetics industry may also be employed, e.g. dyestuff pigments, pearl gloss pigments, colloid stabilizers, UV stabilizers. and/or antibacterially active substances.

The method of manufacturing the nail lacquer may be done by a conventional method of lacquer formulation, such as one of those described, e.g., in Kirk-Othmer 3rd Ed., 1979, loc. cit., Vol. 6, up. 427–445.

In a preferred embodiment, the film former is first taken up by (or mixed to swelling with) a component A of the solvent mixture, and then in a second step the active principles (antimycotic and urea) and any plasticizers and/or other additives are added, in dissolved form in a component B of the solvent mixture. Particularly preferred substances for component A are ketones and esters (more particularly acetone—if the film former is cellulose acetate), and for component B alcohols (more particularly ethanol, if the antimycotic is clotrimazole, employed along with urea).

The inventive nail lacquer has an onycholytic and antimycotic action, wherewith the active principles (urea and an antimycotic) are liberated from the lacquer in such a way that the healthy parts of the nail do not undergo any substantial keratolysis, and thus it is possible to achieve localized topical treatment of onychomycosis with maximum retention of the nail substance.

The lacquer preparates have good application properties, and dry rapidly to a smooth, glossy film, having a white color in the case of urea-containing formulations, because of the high content of urea and solids. Locally controlled application of the nail lacquer is advantageous, because if the application is not carefully circumscribed (e.g. as when a high-urea preparate is applied in ointment form) the high urea content leads to keratolytic attack upon the skin surrounding the nail.

Liberation studies showed that both urea and the antimycotic are liberated from the lacquer at the desired dose rates. The plasticizers which may be added serve to promote the liberation of the urea and the antimycotic; however, if plasticizers are present in high proportions they are detrimental to the properties of the lacquer, rendering it tacky.

A further advantage is that the active principles (urea and the antimycotic) do not need to be administered systemically, e.g. orally or intravenously.

Having generally described this invention, a further understanding can be obtained by reference to certain specific examples which are provided herein for purposes of illustration only and are not intended to be limiting unless otherwise specified.

In order to treat onychomycosis, a nail lacquer according to the present invention is applied to the surface of the nail to be treated. The nail lacquer is applied to the nail to be treated and is left of the surface of the nail. The treatment is repeated as necessary, until the affected area to be treated healthy.

The following Examples serve to illustrate the invention.

EXAMPLES

Example 1: Preparation of the Lacquer

The composition of the nail lacquer was as follows:
0.5 g cellulose acetate
0.15 g plasticizer
0.28 g urea
0.10 g clotrimazole,
as a solid incorporated into the following fluid mixture:
3.10 g ethanol (90 vol. %)
5.90 g acetone.

First, the cellulose acetate was taken up by the acetone. Then the active principles (urea and clotrimazole) along with the plasticizer were added, as an ethanol solution.

Example 2: Choice of Suitable Solvent System

There are particular criteria for the choice of a suitable solvent system: It must provide sufficient swelling of the film former, must sufficiently dissolve the active principles to be employed (urea and the antimycotic), and should provide a reasonable drying time of the nail lacquer. The solvent system was chosen and optimized based on a determination of urea solubility and volatility (see Rothemann, K., 1969, "Das grosse Rezeptbuch der Haut- und Koerperpflegemittel", pub. Dr. Alfred Huethig Verlag publishers, Heidelberg). The optimum system was found to comprise acetone and ethanol (the latter as 90 vol. % ethanol with 10 vol. % water), in mixture proportions 70–50 wt. % acetone, 30–50 wt. % ethanol.

Example 3: Selection of the Plasticizer and Liberation of the Active Principles (Urea and Clotrimazole)

Triacetin, propylene glycol, castor oil, and dibutyl phthalate were tested as plasticizers. Regarding outward characteristics, all of the lacquers could be evaluated as good, but there were major differences in the liberation of the active principles (urea and clotrimazole) (see Tables 1a and 1b).

TABLE 1a

Liberation of urea from lacquer preparates, as a function of the type of plasticizer used.

| Plasticizer | Urea Liberation | | |
|---|---|---|---|
| | % | μg | mmolar |
| Triacetin | 0.76 ± 0.05 | 11.4 | 21.39 |
| Propyleneglycol | 0.40 ± 0.17 | 6.0 | 11.26 |
| Castor Oil | 0.20 ± 0.08 | 3.0 | 5.63 |
| Dibutylphthalate | 4.42 ± 0.91 | 66.3 | 124.39 |

TABLE 1b

Clotrimazole liberation from lacquer preparates, as a function of the plasticizer used.

| Plasticizer | Clotrimazol Liberation | | | | | |
|---|---|---|---|---|---|---|
| | Membrane | | | | | |
| | 1st % | 2nd % | 3rd % | Total % | μg | mmolar |
| Triacetin | 4.55 ±0.82 | 2.90 ±0.21 | 2.58 ±0.10 | 10.03 ±0.81 | 5.0 | 1.64 |
| Propyleneglycol | 4.10 ±0.54 | 3.70 ±0.29 | 2.46 ±0.73 | 10.26 ±0.62 | 5.1 | 1.68 |
| Castor Oil | 13.96 ±0.88 | 6.42 ±1.15 | 4.70 ±1.21 | 25.10 ±1.79 | 12.6 | 4.10 |
| Dibutylphthalate | 5.95 ±0.19 | 5.28 ±0.15 | 3.95 ±0.58 | 15.18 ±0.67 | 7.6 | 2.48 |

The studies to determine urea- and clotrimazole liberation were carried out with a multimembrane model (see Neubet, R., and Wohlrab, W., 1990 Acta Pharm. Technol., 36, 197), under modified conditions. The membranes used were dodecanol-collodium membranes; test duration was 14 hr. Because of the solvent present in the lacquer formulation, the lacquer could not be applied directly onto the membrane, but was applied to an aluminum foil in a field 2×2 cm which after complete drying was durably pressed onto the membrane in a cell. The amount of lacquer applied was about 5 mg. Because variations in this regard were unavoidable, the evaluation was based on the percent of active principle which was liberated to the membrane (as a percentage of the amount of lacquer applied); the standard deviation over at least 4 parallel tests was given (see Tables 3a and 3b). The data in terms of micrograms and molar concentration were arrived at by calculating the mean values, based on the proportions of urea and antimycotic in 5 mg of lacquer.

Urea Analysis

The urea was extracted from the membrane by agitating 30 min with 4.0 ml water. Samples of 2.0 ml were treated with 1.0 ml of a 0.1% aqueous solution of diacetylmonoxime, 0.5 ml of a solution of N-(1-naphthyl)ethylenediammonium dichloride (0. 005 mol/l) containing 0.05% sodium bicarbonate ($NaHCO_3$), and 0.5 ml concentrated sulfuric acid. After a reaction time of 10 min in a boiling water bath, 0.25 ml of 1% potassium persulfate solution was added immediately. After color development over a period of 10–15 min, the samples were measured spectrophotometrically at 564 nm.

Clotrimazole Analysis

After extraction of the medicine from the membrane by agitating 30 min with 4.0 ml chloroform, 5.0 ml of a color reagent was added, comprised of 100 mg methyl orange in 100 ml boric acid solution (0.5 mol/l) which reagent had been freshly prepared and filtered. After agitation 5 min, 300 μl sulfuric acid reagent was added to 2.0 ml of the organic phase. This sulfuric acid reagent was comprised of 2.0 ml concentrated . sulfuric acid +100.0 ml ethanol. The mixture was evaluated spectrophotometrically at 520 nm.

Results

The distribution and liberation varied, as a result of the different physicochemical characteristics of urea and clotrimazole. Dibutyl phthalate liberated 6 to 22 times more urea than the other plasticizers (Table 1a). Castor oil was the plasticizer with which the most antimycotic agent was liberated (Table 1b). For optimal therapy, for which the critical factor is successful onycholysis, the formulation with dibutyl phthalate as the plasticizer was selected.

After successful removal of the affected nail material it is then possible to employ a urea-free lacquer with optimized antimycotic concentration, for the remaining nail material which is still healthy.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patents of the United States is:

1. A nail lacquer (nail polish) for treatment of onychomycosis, comprising:
   a) a polymeric film forming agent,
   b) at least one antimycotically active substance,
   c) urea; and
   d) a solvent which comprises
      i) 50–70 wt. % of acetone; and
      (ii) 30–50 wt. % of 90 volume % aqueous ethanol;
   wherein in a first step, said polymeric film forming agent is dissolved in said acetone component of said solvent, and then in a second step, said antimycotically active substance and said urea are added to said polymeric film forming agent, in dissolved form in said aqueous ethanol; and
   wherein following topical application and drying of said nail lacquer, the antimycotically active substance and said urea are liberated from the lacquer.

2. The nail lacquer of claim 1, wherein said film forming agent is a cellulose derivative.

3. The nail lacquer of claims 2 or 1, further comprising 5–30 wt. %, based on the weight of the non-volatile components of a plasticizer, selected from the group consisting of phthalic acid ester, glycol, triacetin, camphor, castor oil and a mixture thereof.

4. The nail lacquer of claims 2 or 1, wherein said antimycotically active substance is clotrimazole.

5. The nail lacquer of claims 2 or 1, wherein said antimycotically active substance is present in the amount of 5–30 wt %, based on the weight of the non-volatile components.

6. The nail lacquer of claims 2 or 1, wherein said urea is present in the amount of 15–60 wt. %, based on the weight of the non-volatile components.

7. The nail lacquer of claim 3, wherein said plasticizer is dibutyl phthalate.

8. The nail lacquer of claim 3, further comprising 10-20 wt. %, based on the weight of the non-volatile components of a plasticizer, selected from the group consisting of phthalic acid ester, glycol, triacetin, camphor, castor oil and a mixture thereof.

9. The nail lacquer of claim 5, wherein said antimycotically active substance is present in an amount of 10-20 wt. %, based on the weight of the non-volatile components.

10. The nail lacquer of claim 6, wherein said urea is present in an amount of 20-50 wt. % based on the weight of the non-volatile components.

11. The nail lacquer of claim 2, wherein said film forming agent is selective from the group consisting of cellulose acetate phthalate, cellulose acetate butyrate, cellulose acetate propionate, cellulose nitrate, cellulose sulfate, ethylcellulose, and cellulose acetate and a mixture thereof.

12. The nail lacquer of claim 1, wherein said antimycotically active substance is selected from the group consisting of tioconazole, econazole, oxiconazole, miconazole, clotrimazole and a mixture thereof.

13. A method of treating onychomycosis comprising applying the nail lacquer of claim 1 on the surface of a nail to be treated.

* * * * *